US010765670B2

(12) United States Patent
Mouthon et al.

(10) Patent No.: US 10,765,670 B2
(45) Date of Patent: Sep. 8, 2020

(54) USE OF ANTI-CONNEXIN AGENTS FOR ENHANCING THE THERAPEUTIC EFFECT OF ACETYLCHOLINESTERASE INHIBITORS

(71) Applicant: COMMISSARIAT A L'ENERGIE ATOMIQUE ET AUX ENERGIES ALTERNATIVES, Paris (FR)

(72) Inventors: Franck Mouthon, Boulogne Billancourt (FR); Mathieu Charveriat, Issy les Moulineaux (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/903,662

(22) Filed: Feb. 23, 2018

(65) Prior Publication Data

US 2018/0177773 A1 Jun. 28, 2018

Related U.S. Application Data

(63) Continuation of application No. 14/355,153, filed as application No. PCT/EP2012/071631 on Oct. 31, 2012, now abandoned.

(30) Foreign Application Priority Data

Oct. 31, 2011 (EP) .................................... 11306407

(51) Int. Cl.
*A61K 31/445* (2006.01)
*A61P 25/28* (2006.01)
*A61K 31/49* (2006.01)
*A61K 45/06* (2006.01)
*A61K 31/196* (2006.01)
*A61K 31/19* (2006.01)

(52) U.S. Cl.
CPC ............ *A61K 31/445* (2013.01); *A61K 31/19* (2013.01); *A61K 31/196* (2013.01); *A61K 31/49* (2013.01); *A61K 45/06* (2013.01); *A61P 25/28* (2018.01)

(58) Field of Classification Search
None
See application file for complete search history.

(56) References Cited

U.S. PATENT DOCUMENTS

| 8,021,701 B1 | 9/2011 | Perry |
| 2004/0116406 A1 | 6/2004 | Opitz et al. |
| 2006/0194723 A1 | 8/2006 | Rabinoff |
| 2008/0021085 A1 | 1/2008 | Koo et al. |
| 2011/0172188 A1 | 7/2011 | Mouthon et al. |

FOREIGN PATENT DOCUMENTS

| CN | 101991859 A | 3/2011 |
| EP | 1602367 A1 | 12/2005 |
| WO | WO 99/26627 A1 | 6/1999 |
| WO | WO 2004/091522 A2 | 10/2004 |

OTHER PUBLICATIONS

Alldredge, "Clinical connexions," Journal of Clinical Pathology, vol. 61, 2008, (published online May 12, 2008), pp. 885-890.
Bai et al., "Block of Specific Gap Junction Channel Subtypes by 2-Aminoethoxydiphenyl Borate (2-APB)," The Journal of Pharmacology and Experimental Therapeutics, vol. 319, No. 3, 2006, pp. 1452-1458.
Béracochéa et al., "Impairment of Spontaneous Alternation Behavior in Sequential Test Procedures Following Mammillary Body Lesions in Mice: Evidence for Time-Dependent Interference-Related Memory Deficits," Behavioral Neuroscience, vol. 101, No. 2, 1987, pp. 187-197.
Béracocháet al., "Improvement of episodic contextual memory by S 18986 in middle-aged mice: comparison with donepezil," Psychopharmacology, vol. 193, 2007, (published online Mar. 24, 2007), pp. 63-73.
Bergman et al., "Successful Use of Donepezil for the Treatment of Psychotic Symptoms in Patients With Parkinson's Disease," Clinical Neuropharmacology, vol. 25, No. 2, 2002, pp. 107-110.
Birks, "Cholinestorase inhibitors for Alzheimer's disease (Review)," The Cochrane Library, Issue 1, 2006, pp. 1-99.
Bontempi et al., "Cognitive Enhancing Properties and Tolerability of Cholinergic Agents in Mice: A Comparative Study of Nicotine, Donepezil, and SIB-1553A, a Subtype-Selective Ligand for Nicotinic . . . ," Neuropsychopharmacology, vol. 28, 2003, (published online Apr. 2, 2003), pp. 1235-1246.
Burt, et al., "Volatile anesthetics block intercellular communication between neonatal rat myocardial cells," Circulation Research, vol. 65, No. 3, 1989, pp. 829-837.
Chaytor et al., "Peptides homologous to extracellular loop motifs of connexin 43 reversibly abolish rhythmic contractile activity in rabbit arteries," Journal of Physiology, vol. 503, No. 1, 1997, pp. 99-110.
Dahl et al., "Attempts to Define Functional Domains of Gap Junction Proteins with Synthetic Peptides," Biophysical Journal, vol. 67, Nov. 1994, pp. 1816-1822.
Dhein, "Pharmacology of gap junctions in the cardiovascular system," Cardiovascular Research, vol. 62, 2004, pp. 287-298.
Fabrizi et al., "Charcot-Marie-Tooth disease type 2E, a disorder of the cytoskeleton," Brain, vol. 130, 2007, pp. 394-403.
Figueroa et al., "Histamine reduces gap junctional communication of human tonsil high endothelial cells in culture," Microvascular Research, vol. 68, 2004, (available online Aug. 27, 2004), pp. 247-257.
Galderisi et al., "Predicting Response to Antipsychotics by Electrophysiological Indices," Methods and Findings in Experimental and Clinical Pharmacology, vol. 24, Suppl. D, 2002, pp. 79.

(Continued)

Primary Examiner — Bong-Sook Baek
(74) Attorney, Agent, or Firm — Birch, Stewart, Kolasch & Birch, LLP

(57) ABSTRACT

This invention relates to improvements in therapeutic neurological and neuropsychic treatments using acetylcholinesterase inhibitors. More specifically, the invention enables the effects of the reversible acetylcholinesterase inhibitor donepezil to be potentiated by certain molecules, referred to here as connexin-blocking agents. Said connexin-blocking agent is preferably meclofenamic acid.

7 Claims, 3 Drawing Sheets

(56) References Cited

OTHER PUBLICATIONS

Gasparini et al., "Non-steriodal anti-inflammatory drugs (NSAIDs) in Alzheimer's disease: old and new mechanisms of action," Journal of Neurochemistry, vol. 91, 2004, pp. 521-536.

Gauthier, et al., "Functional, Cognitive and Behavioral Effects of Donepezil in Patients with Moderate Alzheimer's Disease," Current Medical Research and Opinion, vol. 18, No. 6, 2002, pp. 347-354.

Giepmans, "Gap junctions and connexin-interacting proteins," Cardiovascular Research, vol. 62, 2004, pp. 233-245.

Guan et al., "The Sleep-Inducing Lipid Oleamide Deconvolutes Gap Junction Communication and Calcium Wave Transmission in Glial Cells," The Journal of Cell Biology, vol. 139, No. 7, Dec. 29, 1997, pp. 1785-1792.

Hanseeuw et al., "Increased sensitivity to proactive interference in amnestic mild cognitive impairment is independent of associative and semantic impairment," Brain and Cognition, vol. 72, 2010, (available online Nov. 10, 2009) pp. 325-331.

Harks et al., "Fenamates: A Novel Class of Reversible Gap Junction Blockers," The Journal of Pharmacology and Experimental Therapeutics, vol. 298, No. 3, 2001, pp. 1033-1041.

Hofer et al., "Visualization and Functional Blocking of Gap Junction Hemichannels (Connexons) With Antibodies Against External Loop Domains in Astrocytes," GLIA, vol. 24, 1998, pp. 141-154.

Johannsen et al., "Assessing Therapeutic Efficacy in a Progressive Disease: A Study of Donepezil in Alzheimer's Disease," CNS Drugs, vol. 20, No. 4, 2006, pp. 311-325.

Joo et al., "Mefenamic Acid Shows Neuroprotective Effects and Improves Cognitive Impairment in in Vitro and in Vivo Alzheimer's Disease Models," Molecular Pharmacology, vol. 69, No. 1, Jan. 2006 (published online before print Oct. 13, 2005), pp. 76-84.

Lai-Cheong et al., "Genetic Diseases of Junctions," Journal of Investigative Dermatology, vol. 127, 2007, pp. 2713-2725.

Locke et al., "Reversible Pore Block of Connexin Channels by Cyclodextrins," The Journal of Biological Chemistry, vol. 279, No. 22, May 28, 2004 (available online Mar. 23, 2004), pp. 22883-22892.

Mcgleenon et al., "Acetylcholinesterase inhibitors in Alzheimer's disease," British Journal of Clinical Pharmacology, vol. 48, 1999, pp. 471-480.

Meyer et al., "Inhibition of Gap Junction and Adherens Junction Assembly by Connexin and A-CAM Antibodies," The Journal of Cell Biology, vol. 119, No. 1, Oct. 1, 1992, pp. 179-189.

Nieoullon, "Les anticholinesterasiques dans la maladie d'Alzheimer: reflexions sur leurs modalités d'action potentielles et les effets thérapeutiques," Psychologie & Neuropsychiatrie du Vieillissement, vol. 8, No. 2, Jun. 2010, pp. 123-131.

Pan et al., "Screening of gap junction antagonists on dye coupling in the rabbit retina," Visual Neuroscience, vol. 24, No. 4, 2007, pp. 609-618.

Postma et al., "Acute loss of Cell-Cell Communication Caused by G Protein-coupled Receptors: A Critical Role for c-Src," The Journal of Cell Biology, vol. 140, No. 5, Mar. 9, 1998, pp. 1199-1209.

Salameh et al., "Pharmacology of Gap junctions. New pharmacological targets for treatment of arrhythmia, seizure and cancer?," Biochimica et Biophysica Acta, vol. 1719, 2005, (available online Sep. 21, 2005), pp. 36-58.

Scemes, "Modulation of Astrocyte P2Y1 Receptors by the Carboxyl Terminal Domain of the Gap Junction Protein Cx43," Glia, vol. 56, 2008, (available online Nov. 7, 2007), pp. 145-153.

Shaw et al., "Microtubule Plus-End-Tracking Proteins Target Gap Junctions Directly from the Cell Interior to Adherens Junctions," Cell, vol. 128, Feb. 9, 2007, pp. 547-560.

Spowart-Manning et al., "The T-maze continuous alternation task for assessing the effects of putative cognition enhancers in the mouse," Behavioural Brain Research, vol. 151, 2004, pp. 37-46.

Srinivas et al., "Closure of Gap Junction Channels by Arylaminobenzoates," Molecular Pharmacology, vol. 63, No. 6, 2003, pp. 1389-1397.

Srinivas et al., "Quinine blocks specific gap junction channel subtypes," Proceedings of the National Academy of Sciences of the United States of America, vol. 98, No. 19, Sep. 11, 2001, pp. 10942-10947.

Srinivas, "Pharmacology of Connexin Channels," Connexins: A Guide, Chapter 8, 2009, pp. 207-224.

Tronche et al., "Pharmacological modulation of contextual "episodic-like" memory in aged mice," Behavioural Brain Research, vol. 215, 2010, (available online Apr. 10, 2010), pp. 255-260.

Walther et al., "Improved Learning and Memory in Aged Mice Deficient in Amyloid β-Degrading Neutral Endopeptidase," PLoS One, vol. 4, No. 2, Feb. 2009, pp. 1-11.

Yao et al., "Nitric Oxide-Mediated Regulation of Connexin43 Expression and Gap Junction Intercellular Communication in Mesangial Cells," Journal of the American Society of Nephrology, vol. 16, 2005, pp. 58-67.

Yao et al., "PDGF regulates gap junction communication and connexin43 phosphorylation by PI 3-kinase in mesangial cells," Kidney International, vol. 57, 2000, pp. 1915-1926.

Extended European Search Report, dated Jan. 30, 2019, for European Application No. 18195298.7.

Joo et al., "Mefenamic Acid Shows Neuroprotective Effects and Improves Cognitive Impairment in in Vitro and in Vivo Alzheimer's Disease Models", Molecular Pharmacology, vol. 69, No. 1, 2006, pp. 76-84.

Juszczak et al., "Properties of gap junction blockers and their behavioural, cognitive and electrophysiological effects: Animal and human studies", Progress in Neuro-Psychopharmacology & Biological Psychiatry, vol. 33, 2009 (available online Jan. 1, 2009), pp. 181-198.

Van Essen et al., "Anti-malaria drug mefloquine induces motor learning deficits in humans", Frontiers in Neuroscience, vol. 4, No. 191, Nov. 2010, p. 1-8 (8 pages).

USE OF ANTI-CONNEXIN AGENTS FOR ENHANCING THE THERAPEUTIC EFFECT OF ACETYLCHOLINESTERASE INHIBITORS

CROSS-REFERENCE TO RELATED APPLICATIONS

This application is a Continuation of copending application Ser. No. 14/355,153, filed on Apr. 29, 2014, which is the National Phase under 35 U.S.C. § 371 of International Application No. PCT/EP2012/071631, filed on Oct. 31, 2012, which claims the benefit under 35 U.S.C. § 119(a) to Patent Application No. 11306407.5, filed in Europe on Oct. 31, 2011, all of which are hereby expressly incorporated by reference into the present application.

This invention relates to improvements in therapeutic neurological and neuropsychic treatments using acetylcholinesterase inhibitors. More specifically, the invention enables the effects of acetylcholinesterase inhibitors to be potentiated by certain molecules, referred to here as connexin-blocking agents.

Cognitive disorders are a category of mental health disorders that primarily affect learning, memory, perception, and problem solving, and include amnesia, dementia, and delirium. Causes vary between the different types of disorders but most include damage to the memory portions of the brain. Treatments depend on how the disorder is caused. Medication and therapies are the most common treatments; however, for some types of disorders such as certain types of amnesia, treatments can suppress the symptoms but there is currently no cure.

Enhancement of cognitive function occurs when the action of Acetylcholine (Ach) is increased via inhibition of its metabolizing enzymes, principally the acetylcholinesterase enzyme (AChE). Accordingly, the strategy of increasing cholinergic activity to restore cognitive functions has been a primary and enduring therapeutic tactic.

Nowadays, several acetylcholinesterase inhibitors (ChEIs, or AChEIs or anti-cholinesterase agents) have been shown to reduce the rate at which acetylcholine is broken down and hence increase its concentration in the brain (thereby combating the loss of ACh caused by the death of the cholinergic neurons). Acetylcholinesterase inhibitors enhance neuronal transmission by increasing the availability of ACh in muscarinic and nicotinic receptors. According to findings of some researchers, these ChEIs may have psychotropic effects and may play an important role in controlling neuropsychiatric and behavioral disturbances in patients with cognitive disorders. These agents may also contribute to the management of other disorders with cholinergic system abnormalities and neuropsychiatric symptoms such as visual hallucinations.

Donepezil is a well-known AChEI. It has been proposed for treating numerous cognitive disorders (Lewy body dementia, vascular dementia, sleep apnea, mild cognitive impairment, schizophrenia, CADASIL syndrome, attention deficit disorder, postcoronary bypass cognitive impairment, cognitive impairment associated with multiple sclerosis, and Down syndrome). It has been approved for treating mild to moderate Alzheimer's disease.

Alzheimer's disease (AD) is an irreversible, progressive disorder in which brain cells (neurons) deteriorate, resulting in the loss of cognitive functions, primarily memory, judgment and reasoning, movement coordination, and pattern recognition. In advanced stages of the disease, all memory and mental functioning may be lost. The death of the nerve cells occurs gradually over a period of years. It is associated with senile dementia which is the mental deterioration (loss of intellectual ability) that is associated with old age. They are currently 5.3 million people with AD in the United States, and more than half of these individuals will likely be categorized as having moderate or severe disease. These advanced stages of AD extend over a period of several years and are often the most difficult for both patients and caregivers. An important component of the pathophysiology of AD, recognized more than 30 years ago, is degeneration of the cholinergic system. Early histologic studies showing loss of cholinergic activity as AD progresses are supported by several modern lines of investigation using advanced imaging techniques, including positron imaging techniques (PET) and magnetic resonance imaging (MRI). The cholinergic abnormalities seen in AD are not viewed as the cause of the disorder, but cholinergic involvement is significant because it is universal, correlates with cognitive defects, and is one of the few pathophysiologic phenomena that can be addressed with currently approved treatment options.

However, the acetylcholinesterase-inhibitors that have been approved so far (and in particular donepezil), have been less promising therapeutically as they produce only modest improvements in cognitive function and the induced cognitive gain (if any) only lasts few months.

There is therefore an urgent need of new treatments enabling to reduce and/or impair the loss of cognitive symptoms more efficiently and more durably for all patients suffering from cognitive disorders, especially those suffering from Alzheimer in advanced stages.

The present invention fulfills this need by disclosing a new therapeutic product showing improved effects on memory loss than the existing treatments.

DESCRIPTION OF THE INVENTION

Figure 1:
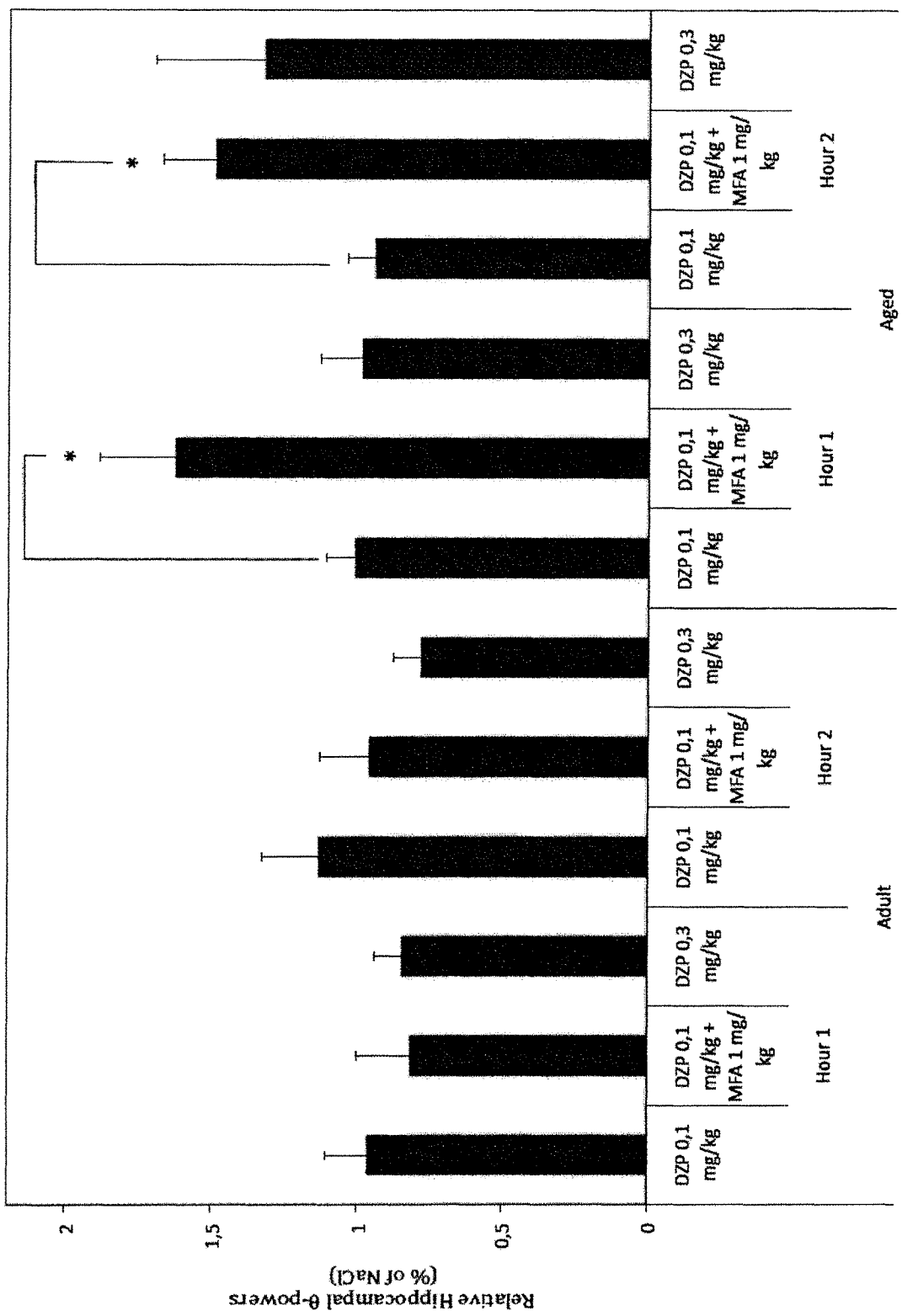
FIG. 1 shows the θ-hippocampal analysis of adult mice (4-5 month old mice—6 first columns) and elderly mice (17-18 month-old mice—6 last columns) after intraperitoneal administration of 0.1 mg/kg or 0.3 mg/kg of donepezil (DZP) associated or not with 1 mg/kg of meclofenamic acid (MFA).

The present Inventors have hereafter demonstrated that the association of Meclofenamic Acid (MFA) with an acetylcholinesterase inhibitor such as donepezil surprisingly results in qualitatively superior preclinical gains compared to higher doses of the acetylcholinesterase inhibitor alone.

Meclofenamic acid has been described as a "connexin-blocking" agent having a non-steroidal anti-inflammatory activity.

In the context of this invention, a "connexin-blocking" agent is a chemical molecule, a protein, a protein fragment or a nucleic acid (for example RNAi) capable of inhibiting the functional activity of connexins, directly and/or indirectly, and more generally any type of intercellular junctions, and/or capable of functionally inhibiting, directly and/or indirectly any cellular activity involving a connexin-type protein. Such an agent can also be referred to as an "anti-connexin molecule".

Various molecules are known for blocking the gap junctions via connexins. Among them, the family of fenamates includes the following compounds: meclofenamic acid, mefenamic acid, flufenamic acid, niflumic acid and tolfenamic acid. These compounds all have a non-steroidal anti-inflammatory activity, but this activity is not responsible for their capacity to block the gap junctions. It has indeed been suggested that the fenamates instead establish a direct interaction with the connexins or with the protein membrane interfaces that may influence the conformation of the connexins and therefore the functional role thereof (Harks E G, *The Journal of Pharmacology and Experimental Therapeutics* 2001 September, 298(3): 1033-41).

Benzoic 2-[(2,6-di-chloro-3-phenyl)amino] acid, more commonly known as meclofenamic acid (MFA), is a non-steroidal anti-inflammatory agent and a peripheral analgesic of the fenamate class, a prostaglandin inhibitor, described among the water-soluble blockers as being one of the most effective for reversibly blocking the gap junctions. In addition, meclofenamic acid is not specific to a type of connexin and is therefore effective for blocking a large number of cerebral connexins (Pan F, *Vis Neurosciences* 2007, July-August; 24(4): 609-18).

Glycyrrhetinic acid derivatives refer to 18-β-glycyrrhetinic acid (BGA) also known as "enoxolone", 18-α-glycyrrhetinic acid and carbenoxolone acid, which are triterpinoid saponins known for inhibiting the 11-hydroxysteroid dehydrogenase enzyme. Moreover, these compounds are capable of very effectively inhibiting the gap junctions (Pan F, *Vis Neurosciences* 2007, July-August; 24(4): 609-18).

Members of the quinine family, such as mefloquine (LARIAM), quinine and quinidine, also have a strong antagonist power on the gap junctions (Srinivas M, *PNAS* 2001, 98: 10942-10947; Pan F, *Vis Neurosciences* 2007, July-August; 24(4):609-18).

Some anesthetic agents, such as halothane, enflurane and isoflurane, have a rapid and reversible gap junction blocking effect (Burt J M, et al, *Circ Research.* 1989; 65: 829-37).

Moreover, oleamide (cis-9-octadecenamide), the first amide of oleic acid, also has an inhibiting action on the connexin molecules 43 and 32 (Guan X. et al, *J. Cell Biol* 1997; 139: 1785-92).

In addition, cyclodextrins (α-cyclodextrin (α-CD), β-cyclodextrin (β-CD) and γ-cyclodextrin (γ-CD)), which are natural cyclical oligosaccharides of α-D-glucopyranose, have proven anti-connexin properties (Locke D. et al, *J. Biol Chem* 2004; 279: 22883-92).

Lipophilic agents and fatty acids such as oleic acid, palmitoleic, decaenoic acid and myristoleic acid, the PKC inhibitor staurosporine, cardiac glycosides such as strophanthidin and ouabin, delta-9-tetrahydrocannabinol, 2-aminoethoxydiphenyl borate acetic acid and propionic acid, 12-O-tetradecanoylphorbol-13-acetate (TPA), 2,3 butandione monoxime, carbachol, noradrenaline, FGF-2, angiotensin-II, Atrial Natriuretic factor ANF, VEGF, 1-oleyl-2-acetyl-sn-glycerol, 11,12-epoxyeicosatrienoic acid, lidocaine, tonabersat, Nexagon and Peptagon (from CoDa Therapeutics) have been also proposed as acutely uncoupling cardiovascular gap junctions (Dhein S., *Cardiovascular Research*, 2004 (62) 287-298).

Finally, 2-aminoethyldiphenyl borate (2-APB) is a compound recently identified as a gap junction-blocking agent (Bai D, *J Pharmacol Exp Ther,* 2006 December; 319(3): 1452-8). This modulator of the inositol 1,4,5-triphosphate receptor however fairly specifically targets certain connexins, such as connexins 26, 30, 36, 40, 45 and 50 (Bai D, *J Pharmacol Exp Ther,* 2006 December; 319(3): 1452-8).

Similarly, other molecules have recently been proposed for blocking the extracellular connexin domain—a domain that is important for the functioning of the gap junctions. It involves in particular antibodies directed against the extracellular connexin domain (Hofer A et al, *Glia* 1998; 24: 141-54; Meyer R A, *J. Cell Biol.* 1992; 119: 179-89) or small peptides mimicking specific sequences conserved by the extracellular loops E1 and E2 of the connexins (Dahl G. et al, *Biophys J,* 1994; 67: 1816-22); in particular, the peptides corresponding to the extracellular sequences include the conserved patterns QPG and SHVR of E1 (Gap26) and the conserved pattern SRPTEK of E2 (Gap27) of the connexins are more effective for blocking the gap junctions (Chaytor A T et al, *J. Physiol* 1997; 503: 99-110).

Moreover, the formation of functional gap junctions can be regulated by means of connexin phosphorylation. Indeed, phosphorylation of certain protein domains of the hexamer sub-units leads to an inhibition in the functionality of the gap junctions, according to the phosphorylation site, by closing the channels or by reducing the presence at the membrane (modification of traffic and half-life of sub-units) (Scemes E, *Glia* 2008 Jan. 15, 56(2): 145-53; Postma F R, *J Cell Biol* 1998 Mar. 9, 140(5): 1199-209; Shaw R M, *Cell* 2007, Feb. 9, 128(3): 547-60; Fabrizi G M, *Brain* 2007 February, 130 (Pt2): 394-403).

Thus, molecules can have an indirect gap junction-blocking effect, via the phosphorylation levels of the connexins. They are in particular: lysophosphatidic acid, thrombin and neuropeptides, such as endothelin (Postma F R, *J Cell Biol* 1998 Mar. 9, 140(5): 1199-209). In a preferred embodiment of the invention, the connexin-blocking agent has an indirect effect on the connexins and the gap junctions, and it is chosen from the group consisting of: lysophosphatidic acid, thrombin and neuropeptides, such as endothelin.

In the context of this invention, the connexin-blocking agents are advantageously chosen from: long-chain alcohols (for example, heptanol and octanol), fenamates (for example, meclofenamic acid, mefenamic acid, flufenamic acid, niflumic acid, tolfenamic acid), arylaminobenzoates, aminosulfonates (for example taurine), glycyrrhetinic acid derivatives (for example, 18-β-glycyrrhetinic acid, 18-α-glycyrrhetinic acid and carbenoxolone), oleamides (for example, cis-9-octadecenamide), or tetraalkylammonium ions and polyamines (such as spermine and spermidine), quinine derivatives (such as mefloquine, quinine, quinidine), 2-ABP, anesthetic agents (halothane, enflurane or isoflurane), cyclodextrins (α-cyclodextrin (α-CD), β-cyclodextrin (β-CD), and γ-cyclodextrin (γ-CD)), antibodies directed against the extracellular domain of the connexins or peptides with conserved patterns mimicking this particular domain (in particular Gap26 and Gap27), oleic acid, palmitoleic acid, decaenoic acid, myristoleic acid, staurosporine, strophanthidin, ouabin, delta-9-tetrahydrocannabinol, 2-aminoethoxydiphenyl borate acetic acid, propionic acid, 12-O-tetradecanoylphorbol-13-acetate (TPA), 2,3 butandione monoxime, carbachol, noradrenaline, FGF-2, angiotensin-II, Atrial Natriuretic factor ANF, VEGF, 1-oleyl-2-acetyl-sn-glycerol, 11,12-epoxyeicosatrienoic acid, lidocaine, tonabersat (SB-220453, (cis-(−)-6-acetyl-4S-(3-chloro-4-fluoro-benzoylamino)-3,4-dihydro-2,2-dimethyl-2H-1-benzopyran-3S-ol), Nexagon and Peptagon (from CoDa Therapeutics). These different molecules are specifically described in the following articles: Srivinas M, Connexins: A Guide, *Humana Press* 2009, Chapter 8, pages 207-224; Srinivas M, *Molecular Pharmacology* 2003 June, 63(6): 1389-97; Harks E G, *The Journal of Pharmacology and Experimental Therapeutics* 2001 September, 298(3): 1033-41; and Salameh A, *Biochimica et Biophysica Acta* 1719 (2005) 36-58; Dhein S., *Cardiovascular Research,* 2004 (62) 287-298.

These compounds are provided as examples, and the invention relates to any molecule having the properties of functional blocking, direct or indirect, of the connexins or gap junctions.

Moreover, it should be noted that the anti-inflammatory molecules can indirectly produce, by their action on the prostaglandin synthase, a structural modification of the connexins (the regulation of the connexin expression levels or of the phosphorylation thereof occurs in particular via PI3K and PKA, themselves dependent on the activity levels of Cox, NO and PG synthetase, targets of anti-inflammatories). This modification, in the sense of a reduction in the presence of the connexins in the junctions, indirectly causes a reduction in the functional activity of the connexins similar to a direct blocking of the connexins. Consequently, the use of these molecules will produce the desired effect (blocking of connexins) and is not an obstacle to combined use at a low dose with psychotropic agents (Yao J, Morioka T & Oite T.: *Kidney Int.* 2000; 57: 1915-26. Yao J, Hiramatsu N, Zhu Y, et al.: *J Am Soc Nephrol.* 2005; 16: 58-67; Figueroa X F, Alvina K, Martinez A D, et al.: *Microvasc Res.* 2004; 68: 247-57 Alldredge B T.: *J Clin Pathol.* May 12, 2008; Lai-Cheong J E, Arita K & McGrath J A.: *J Invest Dermatol.* 2007; 127: 2713-25, and Giepmans B N.: *Cardiovasc Res.* 2004; 62: 233-45).

However, at the low doses involved in the present invention, anti-connexin agents such as meclofenamic acid have no effect on Cox, NO and PG synthetase, and exhibit only an anti-connexin activity which is independent of these enzymes.

All anti-inflammatory molecules having a direct or indirect anti-connexin activity are encompassed in the present invention.

The present invention thus relates to a new combination product containing at least one connexin-blocking agent and an acetylcholinesterase inhibitor, as combination products for simultaneous, separate or sequential use over time, in patients suffering from cognitive disorders.

The connexin-blocking agent can advantageously improve the therapeutic effect of acetylcholinesterase inhibitors prescribed by physicians for treating a patient suffering from cognitive disorders.

The said connexin-blocking agent has been described above. In a preferred embodiment, it is chosen in the group including: meclofenamic acid, mefenamic acid, flufenamic acid, niflumic acid, tolfenamic acid, 18-β-glycyrrhetinic acid also known as "enoxolone", 18-α-glycyrrhetinic acid, carbenoxolone acid, mefloquine, quinine, quinidine, oleamide (cis-9-octadecenamide), oleic acid, palmitoleic acid, decaenoic acid, myristoleic acid, staurosporine, cyclodextrins (α-cyclodextrin (α-CD), β-cyclodextrin (β-CD) and γ-cyclodextrin (γ-CD)), tonabersat (SB-220453, (cis-(−)-6-acetyl-4S-(3-chloro-4-fluorobenzoylamino)-3,4-dihydro-2,2-dimethyl-2H-1 enzopyran-3S-ol), Nexagon and Peptagon (from CoDa Therapeutics).

In a more preferred embodiment, it is chosen in the group including: meclofenamic acid, mefloquine, 18-β-glycyrrhetinic acid and carbenoxolone.

In a rather preferred embodiment, said connexin-blocking agent is meclofenamic acid (MFA).

An "acetylcholinesterase inhibitor" (often abbreviated as "AChEI") or "anti-cholinesterase" is a chemical compound that inhibits the cholinesterase enzyme from breaking down acetylcholine, increasing both the level and duration of action of the neurotransmitter acetylcholine. They occur naturally as venoms and poisons and are used medicinally to treat myasthenia gravis, glaucoma, Alzheimer's disease, Levy body Dementia or as an antidote to anticholinergic poisoning.

The combination product of the invention differs from the prior art in that it contains, as active principles, a cholinergic agent (which is not an acetylcholinergic effector but an acetylcholinesterase inhibitor), and a connexin-blocking agent. In a preferred embodiment, the combination product of the invention contains, as sole active principles, said acetylcholinesterase inhibitor and said connexin-blocking agent. In particular, the combination product preferably does not contain effective amount of a ketone body precursor such as medium chain triglycerides having 5-12 carbon chains. In a preferred embodiment, it does not contain effective amount of phosphodiesterase 7 inhibitor (PDE7). In another preferred embodiment, it does not contain effective amount of axomadol. In another preferred embodiment, it does not contain effective amount of bupropion.

However, the composition can, in addition to the two active principles, comprise any pharmaceutical vehicle, stabilizer, adjuvant and the like as frequently used in the art. Examples of pharmaceutically acceptable vehicles include (but are not limited to): water; aqueous vehicles such as, but not limited to, sodium chloride solution, Ringer's solution, dextrose solution, dextrose and sodium chloride solution, and lactated Ringer's solution; water-miscible vehicles such as, but not limited to, ethyl alcohol, polyethylene glycol, and polypropylene glycol; and nonaqueous vehicles such as, but not limited to, corn oil, cottonseed oil, peanut oil, sesame oil, ethyl oleate, isopropyl myristate, and benzyl benzoate. The skilled person well knows which vehicles can be used.

According to a preferred embodiment, this composition is formulated for oral administration (including buccal cavity or sublingually). Other interesting formulations include formulations for intraperitoneal (i.p), intravenous (i.v.), subcutaneous (s.c.), intramuscular (i.m.), transcutaneous, transdermal, intrathecal and intracranial administrations. Still other formulations include epidural, submucosal, intranasal, ocular cul-de-sac and rectal routes of administration, as well as administration by pulmonary inhalation. The skilled person well knows which vehicles can be used in each kind of composition.

A variety of administration means, including but not limited to capsules, tablets, syrups, creams and ointments, suppositories, patches or any reservoir capable of containing and dispensing the two active principles, can be used for formulating the above-described compositions. The skilled person well knows which vehicles can be used in each case.

In a preferred embodiment, said acetylcholinesterase inhibitor is chosen from Acephate, Azinphos-methyl, Bensulide, Cadusafos, Chlorethoxyfos, Chlorfenvinphos, Chlorpyrifos, Chlorpyrifos-Methyl, Coumaphos, Cyclosarin, Demeton, Demeton-S-Methyl, Diazinon, Dichlorvos, Dicrotophos, Diisopropyl fluorophosphate (Guthion), Diisopropylphosphate, Dimethoate, Dioxathion, Disulfoton, EA-3148, Echothiophate, Ethion, Ethoprop, Fenamiphos, Fenitrothion, Fenthion, Fosthiazate, Isofluorophate, Isoxathion, Malaoxon, Malathion, Methamidophos, Methidathion, Metrifonate, Mevinphos, Monocrotophos, Naled, Novichok agent, Omethoate, Oxydemeton-Methyl, Paraoxon, Parathion, Parathion-Methyl, Phorate, Phosalone, Phosmet, Phostebupirim, Phoxim, Pirimiphos-Methyl, Sarin, Soman, Tabun, Temefos, Terbufos, Tetrachlorvinphos, Tribufos, Trichlorfon, Demecarium, Onchidal, acetylcholinesterase inhibitor chosen among: Aldicarb, Bendiocarb, Bufencarb, Carbaryl, Carbendazim, Carbetamide, Carbofuran, Chlorbufam, Chloropropham, Ethienocarb, Ethiofencarb, Fenobucarb, Fenoxycarb, Formetanate, Furadan, Ladostigil, Methiocarb, Methomyl, Miotine, Oxamyl, Phenmedipham, Pinmicarb, Pirimicarb, Propamocarb, Propham, Propoxur, Ganstigmine, Neostigmine, Phenserine and its enantiomer Posiphen, Physostigmine, Pyridostigmine, Rivastigmine, eptastigmine (heptylphysostigmine), Acotiamide, Ambenonium, Donepezil, Edrophonium, Galantamine, its derivatives SPH 1371, SPH 1373, SPH 1375 and SPH 1286 ((-)N-(3-piperidinopropyl)-N-demethylgalantamine), Huperzine A, its prodrug ZT 1 ((5R,9R)-5-(r-chloro-2-hydroxy-3methoxybenzylidene-amino)-11-ethuidene-7-methyl-1,2,5,6,9,10-hexahydro-5,9-methanocycloocta[b]pyridin-2-one), Minaprine, Tacrine, tolserine (3,4,8b-trimethyl-2,3a-dihydro-1H-pyrrolo[2,3-b]indol-7-yl)N-(2-methylphenyl)carbamate), Zanapezil, ER 127528 (1-(3-fluorobenzyl)-4-[(2-fluoro-5,6-dimethoxy-1-indanone-2-yl) methyl]piperidine hydrochlo-ride), thiatolserine, RS 1259 (N,N-dimethylcarbamic acid 4-[1(S)-(methylamino)-3-(4 nitrophenoxy)propyl]phenyl ester hemifumarate), ipidacrine (NIK-247), velnacrine (9-Amino-1,2,3,4-tetrahydro-1-acridinol), zifrosilone (2,2,2-trifluoro-1-[3-(tri-methylsilyl)phenyl]ethanone), T 82 (2-[2-(1-benzylpiperidin-4-yl) ethyl]-2,3-dihydro-9-methoxy-1H-pyrrolo[3,4-b]quinolin-1-one hemifumerate), CI 1002 (or PD 142676, 1,3-dichloro-6,7,8,9,10,12-hexahydroazepino[2,1-b]-quinazoline), CHF 2060 (N-heptylcarbamic acid 2,4a,9-trimethyl-2,3,4,4a,9,9a-hexahydro-1,2-oxazino[6,5-b]indol-6-yl ester-L-tartrate), MF 268 (N-[8-(cis-2,6-dimethylmorpholin-4-yl)octyl]carbamic acid (3aS,8aR)-1,3a,8-trimethyl-1,2,3,3a,8,8a-hexahydropyrrolo[2,3-b]indol-5-yl ester L-bitartrate hydrate), TV 3326 (N-propargyl-3R-aminoindan-5-yl-ethyl methyl carbamate), Latrepirdine (Dimebolin), (−)-12-amino-3-chloro-9-ethyl-6,7,10,11-tetrahydro-7,11-methanocycloocta[b] quinoline hydrochloride (huperzine X), 3-(2-[1-(1,3-dioxolan-2-ylmethyl) piperidin-4-yl]ethyl)-3,4-dihydro-2H-1,3-benzoxazine-2,4-dione hydro-chloride (E 2030) and the pharmaceutically salts thereof.

Said acetylcholinesterase inhibitor can have reversible or irreversible effects.

In a more preferred embodiment, said acetylcholinesterase inhibitor is an irreversible acetylcholinesterase inhibitor chosen among: Acephate, Azinphos-methyl, Bensulide, Cadusafos, Chlorethoxyfos, Chlorfenvinphos, Chlorpyrifos, Chlorpyrifos-Methyl, Coumaphos, Cyclosarin, Demeton, Demeton-S-Methyl, Diazinon, Dichlorvos, Dicrotophos, Diisopropyl fluorophosphate (Guthion), Diisopropylphosphate, Dimethoate, Dioxathion, Disulfoton, EA-3148, Echothiophate, Ethion, Ethoprop, Fenamiphos, Fenitrothion, Fenthion, Fosthiazate, Isofluorophate, Isoxathion, Malaoxon, Malathion, Methamidophos, Methidathion, Metrifonate, Mevinphos, Monocrotophos, Naled, Novichok agent, Omethoate, Oxydemeton-Methyl, Paraoxon, Parathion, Parathion-Methyl, Phorate, Phosalone, Phosmet, Phostebupirim, Phoxim, Pirimiphos-Methyl, Sarin, Soman, Tabun, Temefos, Terbufos, Tetrachlorvinphos, Tribufos, Trichlorfon, Demecarium, Onchidal and the pharmaceutically salts thereof.

In a more preferred embodiment, said acetylcholinesterase inhibitor is a reversible acetylcholinesterase inhibitor chosen among: Aldicarb, Bendiocarb, Bufencarb, Carbaryl, Carbendazim, Carbetamide, Carbofuran, Chlorbufam, Chloropropham, Ethienocarb, Ethiofencarb, Fenobucarb, Fenoxycarb, Formetanate, Furadan, Ladostigil, Methiocarb, Methomyl, Miotine, Oxamyl, Phenmedipham, Pinmicarb, Pirimicarb, Propamocarb, Propham, Propoxur, Ganstigmine, Neostigmine, Phenserine and its enantiomer Posiphen, Physostigmine, Pyridostigmine, Rivastigmine, eptastigmine (heptylphysostigmine), Acotiamide, Ambenonium, Donepezil, Edrophonium, Galantamine, its derivatives SPH 1371, SPH 1373, SPH 1375 and SPH 1286 ((−)N-(3-piperidinopropyl)-N-demethylgalantamine), Huperzine A, its prodrug ZT 1 ((5R,9R)-5-(r-chloro-2-hydroxy-3methoxybenzylidene-amino)-11-ethuidene-7-methyl-1,2,5,6,9,10-hexahydro-5,9-methanocycloocta[b]pyridin-2-one), Minaprine, Tacrine, tolserine (3,4,8b-trimethyl-2,3a-dihydro-1H-pyrrolo[2,3-b]indol-7-yl)N-(2 methylphenyl) carbamate), (−)-12-amino-3-chloro-9-ethyl-6,7,10,11-tetrahydro-7,11-methanocycloocta[b] quinoline hydrochloride (huperzine X), Zanapezil and the pharmaceutically salts thereof.

In another preferred embodiment, said acetylcholinesterase inhibitor is chosen among: ER 127528 (1-(3-fluorobenzyl)-4-[(2-fluoro-5,6-dimethoxy-1-indanone-2-yl) methyl]piperidine hydrochlo-ride), thiatolserine, RS 1259 (N,N-dimethylcarbamic acid 4-[1 (S)-(methylamino)-3-(4 nitrophenoxy)propyl]phenyl ester hemifumarate), ipidacrine (NIK-247), velnacrine (9-Amino-1,2,3,4-tetrahydro-1-acridinol), eptastigmine (heptylphysostigmine), zifrosilone (2,2,2-trifluoro-1-[3-(tri-methylsilyl)phenyl]ethanone), T 82 (2-[2-(1-benzylpiperidin-4-yl) ethyl]-2,3-dihydro-9-methoxy-1H-pyrrolo[3,4-b]quinolin-1-one hemifumerate), CI 1002 (or PD 142676, 1,3-dichloro-6,7,8,9,10,12-hexahydroazepino[2,1-b]-quinazoline), CHF 2060 (N-heptylcarbamic acid 2,4a,9-trimethyl-2,3,4,4a,9,9a-hexahydro-1,2-oxazino [6,5-b]indol-6-yl ester-L-tartrate), MF 268 (N-[8-(cis-2,6-dimethylmorpholin-4-yl)octyl] carbamic acid (3aS,8aR)-1,3a,8-trimethyl-1,2,3,3a,8,8a-hexahydropyrrolo[2,3-b]indol-5-yl ester L-bitartrate hydrate), TV 3326 (N-propargyl-3R-aminoindan-5-yl-ethyl methyl carbamate) and Latrepirdine (Dimebolin) and the pharmaceutically salts thereof.

In a rather preferred embodiment, said acetylcholinesterase inhibitor is donepezil, a reversible acetylcholinesterase inhibitor, or a pharmaceutically salt thereof.

By "pharmaceutically acceptable salt" is meant for example a salt obtained by mineral or organic acid addition of basic residues such as amines; alkali or organic addition of acidic residues such as carboxylic acids and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts. Pharmaceutically acceptable organic salts includes salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; and combinations comprising one or more of the foregoing salts. Particular salts for donepezil are disclosed in WO 2006/030249.

Donepezil (2,3-dihydro-5,6-dimethoxy-2-[[1-(phenylmethyl)-4-piperidinyl]methyl]-1H-i-nden-1-one) is a piperidine-based reversible, noncompetitive ChEI, which is indicated in the management of patients with Alzheimer's disease of mild to moderate severity. Preliminary observations have suggested the value of donepezil in the amelioration of psychotic symptoms in patients with dementia of the Alzheimer's type (DAT), dementia with Lewy bodies and patients suffering from Parkinson's disease (Bergman et al, *Clin. Neuropharmacol.* 2002; 25(2):107-110, Birks J., *Cochrane Database Syst Rev.* 2006, (1):CD001190, Johanssen P. et al, *CNS drugs* 2006; 20(4):311-25, Gauthier S. et al, *Curr. Med. Res. Opinion* 2002; 18(6):347-54). Donepezil has been proposed for treating numerous other cognitive disorders (vascular dementia, sleep apnea, mild cognitive impairment, schizophrenia, the CADASIL syndrome, attention deficit disorder, post coronary cognitive impairment, cognitive impairment associated with multiple sclerosis, and Down syndrome).

Although some clinical studies have been conclusive, the effect of donepezil is still debated, because the therapeutic effects are small and are not always apparent. The clinical benefit of this cholinergic agent drug is in particular uncertain for patients at advanced stages of the disease for which the amplitude of the improvement is recognized as limited (Nieoullon A., *Psychol. Neuropsychiatr. Vieil.* 2010; 8(2):123-31). More importantly, some patients do not react to these treatments.

The present invention targets in particular a therapeutic substance combination product containing at least one connexin-blocking agent and one acetylcholinesterase inhibitor (AChEI), wherein said connexin-blocking agent is meclofenamic acid and wherein said acetylcholinesterase inhibitor (AChEI) is donepezil or a pharmaceutical salt thereof.

More precisely, the present invention targets a therapeutic substance combination product containing at least one connexin-blocking agent and an acetylcholinesterase inhibitor (AChEI), as combination products for simultaneous, separate or sequential use, as a medicament for treating patients suffering from cognitive disorders, wherein said connexin-blocking agent is meclofenamic acid and wherein said acetylcholinesterase inhibitor (AChEI) is donepezil or a pharmaceutical salt thereof.

This combination product is for example a kit, containing, either in the same recipient or in two distinct recipients, MFA and donepezil or a pharmaceutical salt thereof.

The combination product of the invention contains preferably 1 µg/kg/day to 1 mg/kg/day of donepezil or a pharmaceutical salt thereof. In a preferred embodiment, the combination product of the invention contains between 100 µg/kg/day and 1 mg/kg/day, and even more preferably between 250 µg/kg/day and 1 mg/kg/day of donepezil or a pharmaceutical salt thereof. At these high doses, the combination with MFA enables to prolong the effect of donepezil during time, and to avoid secondary effects that often occur when such high doses are used.

In a preferred embodiment, the combination product of the invention contains between 1 µg/kg/day and 100 µg/kg/day, more preferably between 10 µg/kg/day and 100 µg/kg/day, and even more preferably between 10 µg/kg/day and 40 µg/kg/day of donepezil or a pharmaceutical salt thereof. At these low doses, the combination with MFA enables to obtain a sufficient effect of donepezil without triggering secondary effects.

The anti-inflammatory effect of MFA is observed in vivo at a dose of approximately 5 mg/kg/day (see Wagner C. et al, *Am. J. Physiol. Regul. Integr. Comp. Physiol.* 293 2007; R1781-6). However, when used in the combination product of the invention, the amount of MFA is much lower, and typically comprised between 0.5 µg/kg/day and 0.5 mg/kg/day, more preferably between 25 µg/kg/day and 0.5 mg/kg/day, and even more preferably between 125 µg/kg/day and 0.5 mg/kg/day.

This combination product differs from the prior art in that, due to the very low doses of MFA which are used, it does not affect the accumulation of the Aβ proteins (Aβ$_{38}$, Aβ$_{40}$ or Aβ$_{42}$) and it does not involve the cyclooxygenase (COX) pathway. The use of MFA in the combination of the invention is therefore not related at all with its described role as "non-steroid-anti-inflammatory drug" (NSAID), which is observed at higher doses (typically above 5 mg/kg, see Wagner C. et al, *Am. J. Physiol. Regul. Integr. Comp. Physiol.* 293 2007; R1781-6).

Importantly, it has been demonstrated by the inventors that MFA, especially administrated at a low dose, potentiates donepezil and lead to an unexpected synergistic effect: although it has no effect on its own at this low dose, MFA indeed enhances the effect of donepezil beyond what was thought to be its maximal effect (Bontempi B., et al, *Neuropsychopharmacology* 28 2003; 1235-46). Also, MFA accelerates the donepezil's effect, which is observed as soon as 30 minutes post-treatment, while it is not expected before three-day post-treatment when administered alone (see for example in Joo Y. et al, *Molecular Pharmacology* 2006; 69:76-84).

As used herein, the term «cognitive disorder» means any condition characterized by a deficit in mental activities associated with thinking, learning, or memory. Examples of such disorders include agnosias, amnesias, aphasias, apraxias, deliriums, dementias, and learning disorders. In some cases, the cause of a cognitive disorder may be unknown or uncertain. In other cases, the cognitive disorder may be associated with (that is, be caused by or occur in the presence of) other conditions characterized by damage to or loss of neurons or other structures involved in the transmission of signals between neurons. Hence, cognitive disorders may be associated with neurodegenerative diseases such as Alzheimer's disease, corticobasal degeneration, Creutzfeldt-Jacob disease, frontotemporal lobar degeneration, Huntington's disease, multiple sclerosis, normal pressure hydrocephalus, organic chronic brain syndrome, Parkinson's disease, Pick disease, progressive supranuclear palsy, or senile dementia (Alzheimer type); it may be associated with trauma to the brain, such as that caused by chronic subdural hematoma, concussion, intracerebral hemorrhage, or with other injury to the brain, such as that caused by infection (e.g., encephalitis, meningitis, septicemia) or drug intoxication or abuse; and may be associated with Down syndrome and Fragile X syndrome.

Cognitive disorders may also be associated with other conditions which impair normal functioning of the central nervous system, including psychiatric disorders such as mild cognitive disorder, postcoronary bypass cognitive impairment, CADASIL syndrome, anxiety disorders, dissociative disorders, mood disorders, schizophrenia, and somatoform and factitious disorders; it may also be associated with conditions of the peripheral nervous system, such as chronic pain and neuropathic pain.

Examples of dementias are: AIDS dementia complex, Binswanger's disease, dementia with Lewy Bodies, frontotemporal dementia, multi-infarct dementia, Pick's disease, semantic dementia, senile dementia, sleep apnea in dementia, and vascular dementia. Examples of learning disorders are: Asperger's syndrome, attention deficit disorder, attention deficit hyperactivity disorder, autism, childhood disintegrative disorder, and Rett syndrome. Finally, examples of aphasia are progressive non-fluent aphasia.

In a preferred embodiment, the combination product of the invention enables to treat the particular cognitive disorders chosen from: Alzheimer's disease, Parkinson's disease, vascular dementia and senile dementia.

According to another aspect, this invention also relates to the use of this combination product, simultaneously, separately or sequentially, in patients suffering from cognitive disorders.

In the case of simultaneous use, the two components of the treatment are administered to the patient simultaneously. According to this embodiment of the present invention, the two components can be packaged together, in the form of a mixture, or separately, then mixed spontaneously before being administered together to the patient. More commonly, the two components are administered simultaneously, but separately. They can for example be administered with an interval of time which is typically comprised between few minutes and several hours, preferably between 1 minute and five hours, more preferably between 1 minute and two hours.

In particular, the routes of administration of the two components may be different. The administration can also be performed at different sites. In another embodiment, the two components are administered sequentially or spaced apart over time, for example in the same day or at an interval ranging from several hours to several weeks, or even several months.

The present invention also involves the use of at least one connexin-blocking agent such as MFA for preparing a drug intended to be administered before, at the same time, or after an acetylcholinesterase inhibitor, such as donepezil, in order to treat a patient suffering from cognitive disorders.

According to another aspect, the invention includes the use of at least one connexin-blocking agent such as MFA, for potentiating the effect of an acetylcholinesterase inhibitor such as donepezil in patients suffering from cognitive disorders.

The present invention also targets the use of at least one connexin-blocking agent such as MFA, for potentiating the effect of an acetylcholinesterase inhibitor such as donepezil in patients suffering from cognitive disorders.

According to another aspect, the invention thus includes a connexin-blocking agent such as MFA for use to potentiate the effect of an acetylcholinesterase inhibitor such as donepezil in patients suffering from cognitive disorders. All the embodiments concerning the acetylcholinesterase inhibitor, the connexin-blocking agent and the cognitive disorders are hereby encompassed.

The present invention also targets a method for potentiating the effect of an acetylcholinesterase inhibitor such as donepezil, in patients suffering from cognitive disorders, said method using at least one connexin-blocking agent, for example MFA.

The term "potentiate" in this case means significantly increasing the effects of the cholinergic agent administered before, simultaneously or after the anti-connexin agent. In particular, the combination of the cholinergic agent with the anti-connexin agent makes it possible to enhance the therapeutic effect of said cholinergic agent, to an extend which is higher than that obtained by the cholinergic agent alone, whatever its concentration is considered. A "significant increase" of the effects of the cholinergic agent is obtained for example when this effect is enhanced by at least about 25%, preferably at least about 40% and more preferably by at least about 50% as compared with the effect of the cholinergic agent alone. Said effect can be for example measured by analyzing the EEG profile or the percentage of alternation relative to vehicles in laboratory animals as described in the experimental part below.

This enhanced effect ("potentiation") also enables to reduce the doses at which said cholinergic agent is used, and therefore to limit the potential adverse effects of said cholinergic agent, and/or to reduce the effects of failure and withdrawal.

The invention therefore also relates to the use of at least one connexin-blocking agent, for reducing the doses of said cholinergic agent and/or limiting the adverse effects of said cholinergic agent, and/or reducing the effects of failure and withdrawal.

Donepezil is typically used at a dose comprised between 5 mg to 10 mg per day for an adult individual, which means approximately between 100 µg/kg/day and 200 µg/kg/day. As disclosed above, the combination of the invention enables either to reduce the said doses, typically to less than 100 µg/kg/day and preferably to less than 50 hg/kg/day (for example, the dose of donepezil can be comprised between 1 µg/kg/day and 100 µg/kg/day, preferably between 10 µg/kg/day and 100 µg/kg/day, and more preferably between 10 µg/kg/day and 40 µg/kg/day) or to maximize the effect of donepezil over time without inducing secondary effects (when donepezil is used at higher doses, that is, between 100 µg/kg/day and 1 mg/kg/day, preferably between 100 µg/kg/day and 200 µg/kg/day, or between 250 µg/kg/day and 1 mg/kg/day).

According to a final aspect, the invention describes a method for treating a patient suffering from cognitive disorders, including the administration to said patient of:
  a) at least one acetylcholinesterase inhibitor, and
  b) at least one connexin-blocking agent,
and in which said products a) and b) are administered simultaneously, separately or spread out over time.

All embodiments of this method are as described above.

EXAMPLES

1. Materials and Methods
  1.1. Electro-Encephalographic Recording in Mice.
Electrophysiological effects of donepezil were evaluated by analysis of hippocampal electroencephalographic activity (EEG) as described previously in WO2010/029131. Briefly, the assay is as follows:
  Pre-Implantation of the Electrodes:
  Two groups of male C57bl/6 mice (seven mice from 4 to 5 month old and seven mice from 17 to 18 month old) were pre-implanted with bilateral hippocampal bipolar electrodes under isoflurane anaesthesia. A two-week period of recovery was realized before recordings.
  Injections:
  Different intraperitoneal treatments were performed by circular combination of 7 mice per treatment (donepezil 0.1 and 0.3 mg/kg, meclofenamic 1 mg/kg, donepezil 0.1 mg/kg+MFA 1 mg/kg). The dose of 1 mg/kg of MFA has previously been described as not affecting the electroencephalographic signal in rodents.

EEG Measures:

EEG measures were performed on different batches of awoke mice (previously implanted and tamed) by recordings two hours after injection. The spectral analysis is carried out by Fourier transform (FFT) and allows the calculation of the relative powers for each Hertz and each second. FFT data are then averaged minute by minute and reported to control solvent recording realized on the day before in strictly identical experimental conditions. The spectral powers of two hippocampal electrodes are then averaged between 3 and 12 Hertz and represented hourly.

At day 1, saline was administered intraperitoneally to "adult" or "elderly" mice (n=7), and θ-hippocampal activity was measured for two consecutive hours. On day 2, donepezil alone or in combination with MFA is injected, and θ-hippocampal activity is related to that measured on day 1. Results are shown on FIG. 1 (*: p<0.05 (One-way ANOVA).

1.2. Behavioral Test of Working Memory—T-Maze Protocol in Mice

The alternating sequential test is widely used to assess spatial working memory in mice (Beracochea D. J. and Jaffard R., Behav. Neurosci. 101 (1987) 187-97). Spontaneous alternation is the innate tendency of rodents to alternate their choices to enter into the compartments of arrival of a T-maze device, over successive trials. To alternate during a given trial N, the animal must remember the choice made selectively in test N–1, so the decline in alternating will reflect the phenomenon of oblivion. The response in alternating is performance measure. Sequential alternating assess more specifically the sensitivity to interference, a major factor in oblivion.

The experiment took place in a T-maze (50 cm×10 cm×25 cm). All the subjects (C57bl/6 male mice, 17-18-month old, n=9) were given 7 successive trials separated by a 90-s intertrial interval. To begin a trial, the mouse was placed in the start box for 90 s before the door to the stem was opened. When the subject entered one of the goal arms, the door to that arm was closed. The chosen arm and the time that elapsed between opening the door and the arrival to the end of the chosen arm (task achievement time) were registered. Following a 30-s confinement period in the chosen arm, the animal was removed and placed in the start box for a new trial. Between each test, the unit was cleaned with water and alcohol to avoid olfactory detection. An alternation response was considered each time the subject entered the arm opposite to the one visited on the immediately previous trial. Alternation rate was calculated taking into account the 6 successive trials, and expressed in percentage relative to the maximal alternation rate of 100% (obtained when the subject never returned into the same arm for two consecutive trials).

C57BL/6 mice of 17 to 18 months ("elderly" mice) were intraperitoneally injected with a solution of NaCl (vehicle), donepezil (DZP), meclofenamic acid (MFA) or a combination of these two latter compounds, 30 minutes before T-maze experiment.

Thirty minutes after treatment (NaCl, donepezil, MFA), "elderly" mice are placed in the T-maze device. The percentage of alternation was measured for 7 consecutive trials, 50% corresponding to a random alternation. Results are shown on FIGS. 2 and 3 (**: p<0.01; *: p<0.05 (ANOVA)).

1.3. Statistic Analysis

Statistical analysis was established by SigmaPlot software (Systat Software Inc).

2. Experimental Results 2.1. Study of Donepezil Potentiation by Electroencephalography As it is known that increased electrical activity in the CNS, measured on an electroencephalogram (EEG) reflects in some circumstances the therapeutic benefits of a psychoactive drug (Galderisi S. et al, Methods Find. Exp. Clin. Pharmacol. 24 Suppl D (2002) 79), the effect of the combination donepezil/MFA was evaluated on θ-hippocampal activity for two hours and on two groups of mice ("adult" and "elderly") as shown in FIG. 1.

It has been observed that:

4-5-month old mice do not respond significantly to the administration of donepezil 0.1 mg/kg and 0.3 mg/kg, while recordings of 17-18-month old mouse show during the second hour of recording, an effect of donepezil at 0.3 mg/kg. This is consistent with the different responses to donepezil described between "adult" and "elderly" mice (Tronche C. et al, Behav. Brain. Res. 2010; 215:255-260).

Meclofenamic acid potentiates significantly, during the first and the second hour, the pharmacological effect of donepezil.

Accordingly, EEG showed that, whereas MFA had no effect by its own, the combined treatment with donepezil was more potent than donepezil alone. As revealed by ANOVAs, MFA+donepezil increased theta frequency by more than 50% compared to vehicle and donepezil (0.1 and 0.3 mg/kg) treated mice (n=7 per group; p=0.034).

2.2. Study of Donepezil Potentiation by Behavioral Analysis

Donepezil is a promnesiant molecule described as improving the performance of mice in T-maze devices (Spowart-Manning L., Behav. Brain. Res. 151 (2004) 37-46).

Figure 2:
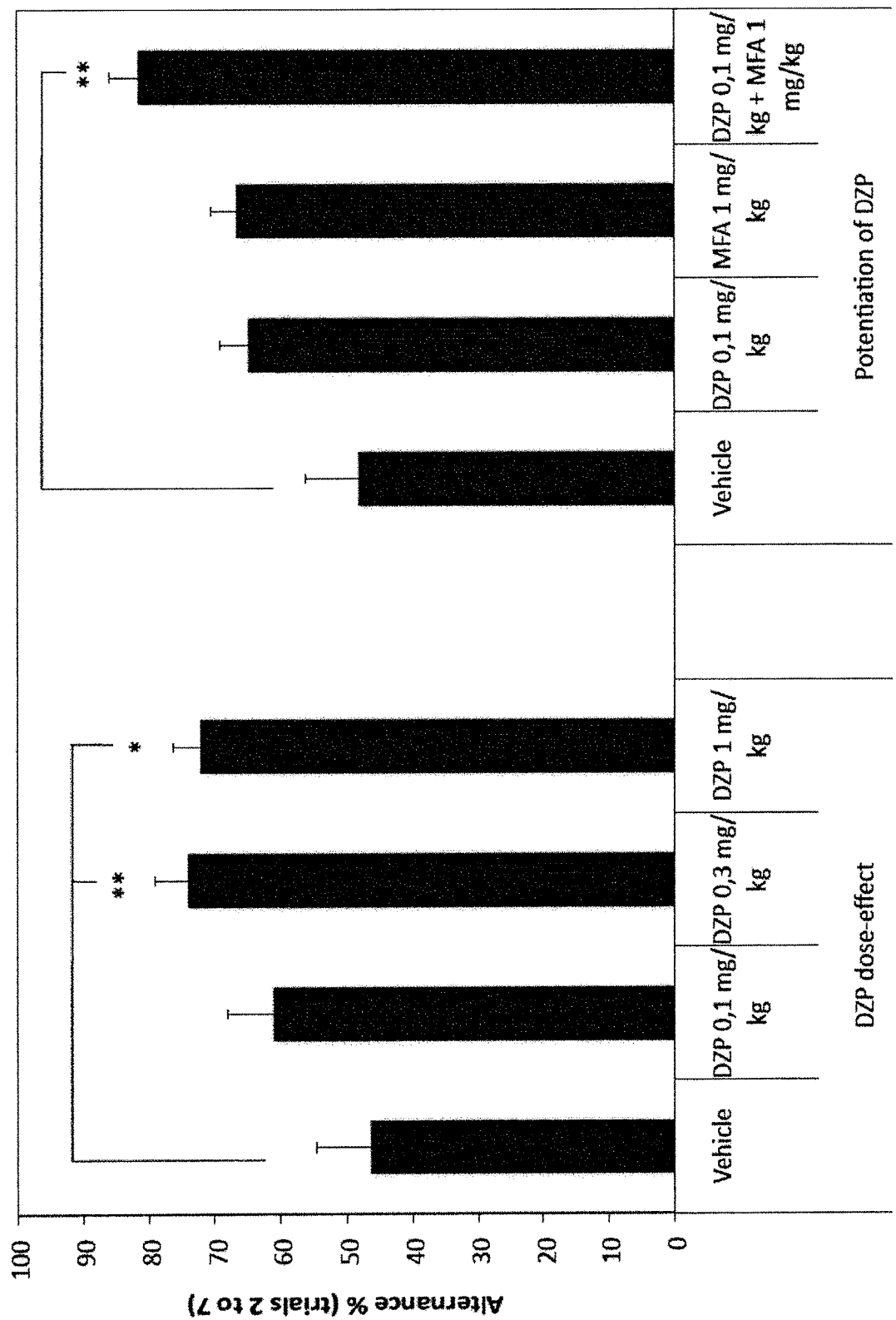
FIG. 2 shows the total alternation of elderly mice (17-18 month-old mice) after intraperitoneal administration of NaCl (vehicle) or of 0.1 mg/kg, 0.3 mg/kg or 1 mg/kg of donepezil alone (DZP) or of 1 mg/kg of meclofenamic acid alone (MFA) or of the combination MFA and DZP (last column). Alternation has been recorded in a T-maze device.

It can be inferred from FIG. 2 that:

Donepezil has a significant promnesiant effect a 0.3 and 1 mg/kg, identified by an increase of alternation due to a recall memory of the choice made in the previous test. This molecule has no significant promnesiant effect 0.1 mg/kg.

Meclofenamic acid has no promnesiant effect significant at 1 mg/kg.

Donepezil at 0.1 mg/kg is potentiated by meclofenamic acid

Figure 3:
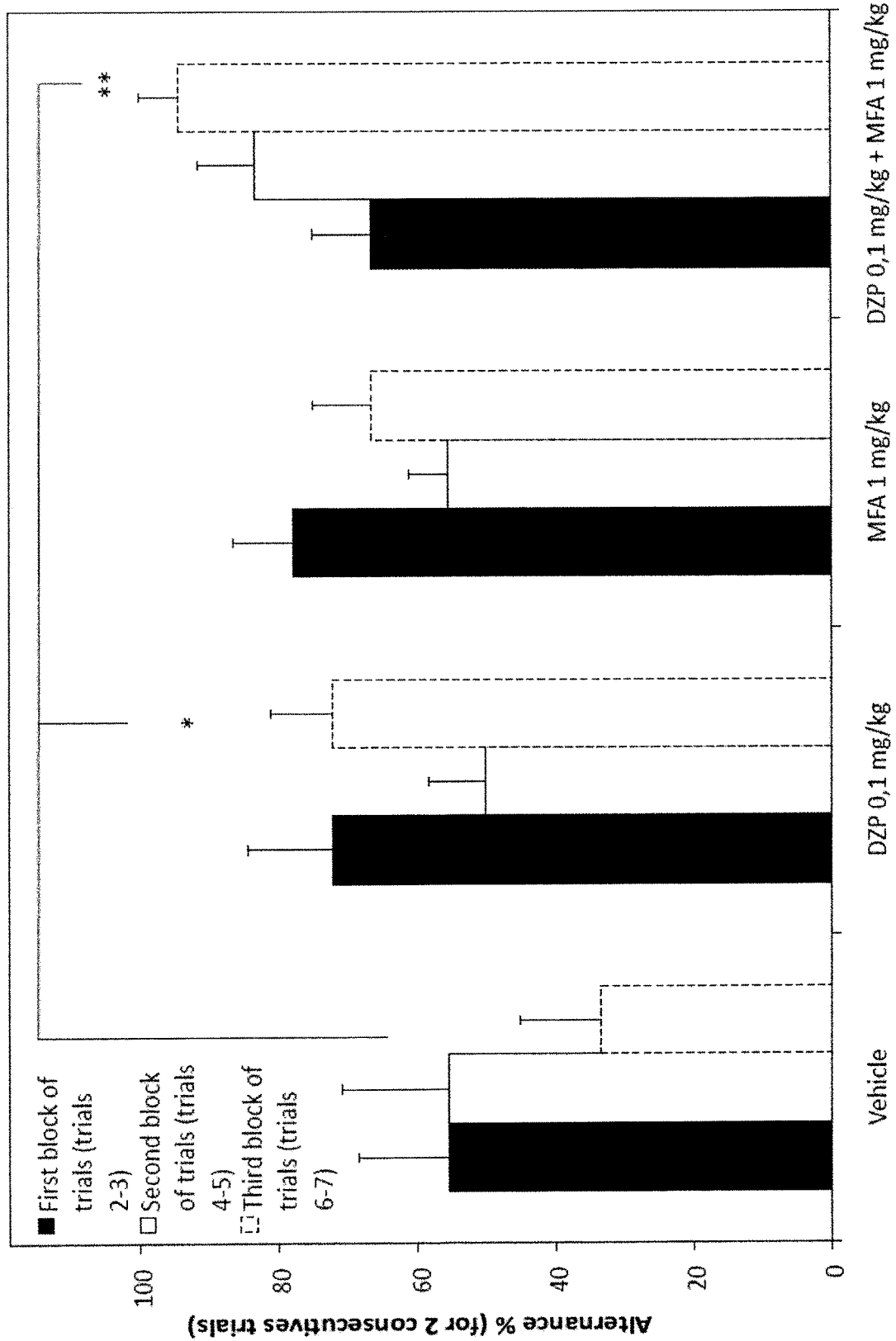
FIG. 3 shows the alternation of "elderly" mice by blocks of two consecutive trials, after intraperitoneal administration of NaCl (vehicle), donepezil alone (0.1 mg/kg), MFA alone (1 mg/kg) and a combination of donepezil and MFA (last group of columns).

The alternation of mice was also analysed with blocks of two trials (Block 1: trials 2 and 3/Block 2: trials 4 and 5/Block 3: trials 6 and 7). The results are shown in FIG. 3:

Meclofenamic acid shows no significant effect on the three blocks of trials.

The performance of control mice ("vehicle") are degraded in the third block, reflecting the effect of memory interference.

Donepezil at 0.1 mg/kg partially counteract the interference phenomenon in the third block of trials.

Meclofenamic acid mainly potentiates the effect of donepezil in the third block, and enhances the recall of memory by reducing the interference phenomenon.

More precisely, the combination with meclofenamic acid allows to reach a higher effect (almost 85%) than the maximal effect observed for donepezil alone, and for a lesser dose of donepezil (0.1 mg/kg, see FIG. 2, last column). In other words, the combined treatment of MFA+donepezil at 0.1 mg/kg was revealed more efficient than highest doses of donepezil alone (i.e. 0.3 and 1 mg/kg) to reverse the age-induced impairment (n=9 per group; p<0.01).

Also, the combination with meclofenamic acid allows to obtain a higher mnesic interference resistance than the one induced by donepezil. This improvement of the effect of donepezil has never been observed so far.

These results are surprising. As a matter of fact, as it can be seen in literature (cf. for example Bontempi B. et al (*Neuropsychopharmacology* 2003; 28; 1235-12460) for the dose of 0.2 mg/kg s.c.) or in the experiments shown above (0.3 mg/kg i.p.), donepezil shows its maximal efficiency at 0.2-0.3 mg/kg (see FIG. 2: around 75% obtained for 0.3 mg/kg and 1 mg/kg of donepezil alone). Higher efficiency was not achievable with donepezil alone, even at higher doses.

Overall Conclusions:

Table 1 below resumes the electroencephalographic (EEG) and behavioural (SA-task) results.

|  | donepezil 0.1 mg/kg | donepezil 0.3 mg/kg | donepezil 0.1 mg/kg + MFA 1 mg/kg | Statistics (ANOVAs) |
|---|---|---|---|---|
| EEG Relative power to vehicles | 1 | 1 | 1.6* | p = 0.034 |
| SA-task relative to vehicles | 35% | 48%** | 68%** | p = 0.0013 |

EEG results are expressed as the relative power of hippocampal theta rhythm of each group compared to vehicles injected mice.
SA-task results are expressed as the mean percentage of alternation relative to vehicles over the seven trails.
*p <0.05;
**p <0.01.

It has been shown for the first time that the electrophysiological activity and promnesiant activity of donepezil is greatly potentiated by meclofenamic acid, which surprisingly allows a maximal pharmacological effect of donepezil.

In addition, meclofenamic acid modifies the pharmacological profile of donepezil, modifying the temporal evolution and intensity of its effects on memory.

It is important to note that MFA, during acute treatment, has no own effect on the preclinical model used herein, so that MFA's activity is thought to be independent from $A\beta$ accumulation:

Independence Between $A\beta$ and NSAID Activity.

The preclinical model used herein (middle-aged wild-type 17-18 month mice) is a pathological model of cognitive impairment which is not characterized by an $A\beta$ accumulation. Indeed, there is no $A\beta$ accumulation in wild-type mice, even beyond 24 months (see FIG. 2 in Walther T. et al, *PLoS One* 2009; e4590), although a cognitive decline is depicted at 17-18 months (see in Beracochea D. et al, *Psychopharmacology* (Berl) 193 2007; 63-73). In addition, no cognitive significant effect of MFA is seen at 1 mg/kg alone, (FIGS. 2 and 3 of this application) while such dose potentiate donepezil.

For its anti-Cox activity MFA is administrated at dose above 5 mg/kg (see in Wagner C. et al, *Am. J. Physiol. Regul. Integr. Comp. Physiol.* 293 2007; R1781-6). However, MFA was used in the present invention at a dose lower than those published for its NSAID activity.

This point constitutes a major difference with prior art documents such as Mc Gleenon et al, *British Journal of Clinical Pharmacology*, 1999; 48, 471-480, and Gasparini L. et al, *Journal of Neurochemistry* 2004; 91, 521-536, since this latter document clearly states that $A\beta$ doses are similar to anti-Cox doses. Thus, the potentiating effect of MFA on donepezil is independent from its potential anti-$A\beta_{1-40}$ ou anti-$A\beta_{1-42}$ effects.

The present invention does not specifically target Alzheimer's disease but all cognitive impairments.

The present invention broadly addresses all cognitive disorders. Such disorders are qualified by the alteration of specific cognitive functions such as attention, memory, language, seen in numerous dementias (Alzheimer's disease, Lewy-body dementia, dementia associated with Parkinson's disease, senile dementia, vascular dementia, hydrocephalia, Korsakoff syndrome, Creutzfeldt-Jakob disease, etc.). Thus, the present invention does not specifically target a disease with $A\beta$ accumulation but rather all types of cognitive impairment, independently from their etiology (as a matter of fact, donepezil is also described at targeting $A\beta$-independent mechanisms such as the cholinergic system).

MFA, administrated—at a low dose and in the above-exemplified preclinical model—potentiates donepezil, which is an unexpected effect:

This effect is not an additive effect but an unexpected synergistic one. As a matter of fact, MFA has no own effect at the tested dose, and donepezil is potentiated beyond its maximal effect (Bontempi B., et al, *Neuropsychopharmacology* 28 2003; 1235-46) (notably with respect to resistance to memory interference, which is altered in human dementia (Hanseeuw B. J., et al, *Brain Cogn.* 72 325-31).

The kinetics of the activity of the combination of the invention is new and unexpected. As a matter of fact, the potentiation of donepezil's efficiency is observed as soon as 30 minutes post-treatment, while effects described in prior art documents (such as Joo Y. et al, Molecular Pharmacology 2006; 69:76-84) are only seen after a three-day treatment.

The invention claimed is:

1. Therapeutic substance combination product containing at least one connexin-blocking agent and one acetylcholinesterase inhibitor (AChEI), wherein said connexin-blocking agent is mefloquine and said acetylcholinesterase inhibitor (AChEI) is donepezil or a pharmaceutical salt thereof, wherein the therapeutic substance combination product is for improving cognitive function in a patient suffering from Alzheimer's disease, Parkinson disease, vascular dementia or senile dementia.

2. A method for improving cognitive function in a patient suffering from Alzheimer's disease, Parkinson disease, vascular dementia or senile dementia, which comprises administering to the patient in need thereof a therapeutic substance combination product containing at least one connexin-blocking agent and an acetylcholinesterase inhibitor (AChEI), wherein said connexin-blocking agent is mefloquine and said acetylcholinesterase inhibitor (AChEI) is donepezil or a pharmaceutical salt thereof.

3. A method of potentiating the effect of donepezil or a pharmaceutical salt thereof in a patient suffering from a cognitive disorder, which comprises coadministering a connexin-blocking agent with said donepezil or a pharmaceutical salt thereof to the patient, wherein said connexin-blocking agent is mefloquine, wherein the cognitive disorder is selected from the group consisting of Alzheimer's disease, Parkinson disease, vascular dementia and senile dementia.

4. The method according to claim 3, wherein the donepezil or a pharmaceutical salt thereof and mefloquine are coadministered simultaneously as a single dosage.

5. The method according to claim 3, wherein the donepezil or a pharmaceutical salt thereof and mefloquine are coadministered simultaneously as separate dosages.

6. The method according to claim 3, wherein the donepezil or a pharmaceutical salt thereof and mefloquine are coadministered separately within 1 minute to 5 hours of each other.

7. The method according to claim 3, wherein the donepezil or a pharmaceutical salt thereof and mefloquine are coadministered separately within 1 minute to 2 hours of each other.

* * * * *